United States Patent [19]

Gordon

[11] Patent Number: 4,758,429
[45] Date of Patent: Jul. 19, 1988

[54] METHOD FOR THE TREATMENT OF ARTHRITIS AND INFLAMMATORY JOINT DISEASES

[76] Inventor: Robert T. Gordon, 4936 W. Estes, Skokie, Ill. 60077

[21] Appl. No.: 794,545

[22] Filed: Nov. 4, 1985

[51] Int. Cl.$^4$ .................... A61B 19/00; A61K 43/00; A61K 49/00
[52] U.S. Cl. ..................................... 424/85; 514/825; 128/1.1; 128/1.3
[58] Field of Search .................. 424/85; 514/825; 128/1.1, 1.3

[56] References Cited

U.S. PATENT DOCUMENTS

| | | | |
|---|---|---|---|
| 4,095,587 | 6/1978 | Ishikawa | 128/1.3 |
| 4,106,488 | 8/1978 | Gordon | 128/1.1 |
| 4,247,406 | 1/1981 | Widder et al. | 424/486 |
| 4,303,636 | 12/1981 | Gordon | 128/1.1 |
| 4,331,654 | 5/1982 | Morris | 424/450 |
| 4,359,453 | 11/1982 | Gordon | 128/1.3 |
| 4,508,119 | 4/1985 | Tukamoto | 128/1.1 |
| 4,590,922 | 5/1986 | Gordon | 128/1.1 |
| 4,606,354 | 8/1986 | Jacob | 128/1.1 |

Primary Examiner—Ronald W. Griffin
Attorney, Agent, or Firm—Lalos & Keegan

[57] ABSTRACT

The present invention describes a method for the treatment of arthritis and joint diseases with diagnostic applications to enhance the treatment process. The process involves the utilization of magnetic or electric dipoles which are present, capable of being induced, or introduced into the cell of the joint and are capable of being activated by an external alternating electromagnetic field. The activation of these magnetic or electric dipoles (particles) allows destruction of the reactive cells and alteration of the intracellular processes with a diminution of the destructive process.

80 Claims, No Drawings

4,758,429

METHOD FOR THE TREATMENT OF ARTHRITIS AND INFLAMMATORY JOINT DISEASES

INTRODUCTION

Arthritis and joint diseases while having some modes of therapy are currently only treated symptomatically. Various medications and drugs are used to decrease the inflammatory response. The mechanism of action of many of these drugs is very poorly understood. When the destructive process has advanced too far, the joint may require surgical intervention and even prosthetic replacement. These prosthesis, while of assistance, do not provide the mobility and feelings inherent in the natural joint.

BACKGROUND OF THE INVENTION

The cause of arthritis and joint disease processes is multiple. Inflammatory joint disease may be related to stimulation of the immune system to the normal joint tissues. Similarly the various collagen diseases can stimulate the inflammatory process i.e. systemic lupus, erythemtosis. Rheumatoid arthritis and osteoarthritis are also examples of disease processes which affect the joint. Infection with bacteria, viruses and fungus can initiate a degenerative process. Tumors both primary and metastatic can invade the joint space and cause destruction. In all of these processes the mechanism is quite similar. Inflammatory cells invade the synovial lining of the joint. A pannus forms and eventually destruction of the joint ensues. The present invention describes a method to stop and/or measureably alter the process before destruction of the joint occurs, thereby preserving the normal joint.

The electromagnetic field interacts with joint tissues in several ways. There are displacement currents due to the drift of electrons, polarization of atoms or molecules to produce dipoles and the interaction with dipoles already present. The coupling of electromagnetic energy to the joint tissues depends on the electrical conductivity ($\delta$) and the dielectric constant ($\epsilon$). The power imparted to the joint issues depends on the square of the amplitude of the field and the coupling constant to the joint tissues. The dielectric properties of the material depend on its composition and structure (i.e. ions, polar molecules, etc.).

In general:

$$\epsilon = \epsilon' - j\epsilon''$$

where
- $\epsilon'$ = real component related to energy stored in the material in electric fields
- $\epsilon''$ = imaginary component related to loss in the form of heat = $\delta 2\pi f \epsilon_o$
- $\delta$ = conductivity so that conductivity is related to the amount of heat loss. Often as there is an increase in frequency, $\epsilon'$ decreases due to less ordering and $\epsilon''$ increases.

In joint tissues a plot of the dielectric constant as a function of frequency often shows three dispersions. Each dispersion is related to a specific phenomenon. The oc dispersion (at $\approx$ 80–100 Hz) is due to the interaction of the charges on the cell surface with the ions in solution and the impedence of the membrane system.

The B dispersion (at $\sim$ 50 KHz) is related to the cell membrane's insulation of the $H_2O$. Above 10 GHz the $\gamma$ dispersion is due to the $H_2O$ and electrolyte solution.

To overcome these problems the common practice is to use a frequency $>>1$ KHz to short out the membrane effects and to deliver energy to the cytoplasm.

Consequently, frequencies greater than 1 KHz and usually greater than 1 MHz are utilized to overcome problems with the cell membrane and deliver energy to the cell. Traditionally, frequencies of 13 MHz or 2450 MHz are used. However, the problem remains that at these high frequencies not only are the joint reactive cells affected but the normal cells are also affected and consequently one is limited in the amount of energy which can be delivered to the reactive joint cells.

The present invention seeks to overcome this problem by modifying the intracellular environment to allow the use of lower frequencies, if possible, and to enhance the effect in the reactive joint cells without affecting the normal cells.

OBJECT OF THE INVENTION

The present invention seeks to prevent the deterioration and/or the destruction of the joint by the use of intracellular particles which are present, capable of being induced or introduced and the use of an alternating electromagnetic field to affect these particles and consequently the joint cells. Through the introduction of intracellular energy, the inflammatory cells can be destroyed or modified to reduce the inflammatory response and prevent or decrease the amount of joint deterioration and/or destruction. A constant magnetic field can be used to impart a dipole to the particles prior to treatment with the alternating electromagnetic field to enhance the effect. In addition, the constant magnetic field can be utilized to modify the behavior of the joint cells and to decrease the degenerative processes.

DETAILED DESCRIPTION OF THE INVENTION

The use of particles to alter the energy level in the cell by the absorption of electromagnetic energy by the particle has been disclosed by the applicant in his U.S. Pat. Nos. 4,106,488; 4,136,683; 4,303,636; and 4,359,453. The present invention seeks to use particles to affect the absorption of energy by the cell itself, and in particular, by reactive cells in the joint, in response to an external alternating electromagnetic field. The implementation of this present treatment method in part utilizes inventive aspects which are the subject of other applications for U.S. Letters Patent by the same inventor as recited hereinafter. For example, a fuller understanding of the technology underlying the Gordon treatment reveals the operation of subtle mechanisms which can themselves become a contributing factor in the course of treatment and are incorporated herein by reference. The selection of particle compositions for use in this present invention as disclosed in the applicant's above described U.S. Patents and as disclosed in copending and commonly assigned Applications, Ser. Nos. 418,298; 464,870 including C.I.P. Ser. No. 522,941, including C.I.P. Ser. Nos. 535,390; 524,844; and 561,811 as well as Application Ser. No. 627,536 of the same inventor, are incorporated herein by reference.

Below several MHz the transmission of energy directly to the cell by an external alternating electromagnetic field is affected by the characteristics of the cell membrane. The charge accumulation on the membrane from intracellular and extracellular fluids accounts for the dielectric polarization of the membrane. The intracellular and extracellular electrolyte solution accounts for the conductance.

In the prior Robert T. Gordon U.S. Pat. Nos. 4,303,636; 4,106,488; and 4,359,455, a high frequency magnetic field is employed to have a direct effect on the particles so that diseased cells can be killed by thermal effects due to hysteresis loss from the particles themselves when the field is relaxed. In contrast to this phenomena, the particles of the present invention are employed to alter the behavior of the reactive cells of the joint such as the magnetic dipoles charge accumulation and conductivity both intra and extra cellularly of a host organism.

The altered environment in turn produces thermal effects (an increase in temperature) when subjected to an alternating magnetic field at relatively low frequencies. These thermal effects are not due to a hysteresis loss from the particles. The frequency range employed according to the present invention which is lower than that of the aforesaid Gordon patents thereby reduces the power requirements. The design and timing of treatment will differ because of the lower frequency ranges employed in the treatment methods of the present invention. One of the additional advantages of the present invention resides in the fact that coil apparatus does not have to be used as was the case in the Gordon patents noted above, the instant invention capable of being practiced inter alia with capacitor plates for developing the frequencies required for treatment.

In the Gordon patents noted above, optimum results were obtained by the metabolism of the particles by the cells. In the present invention effective treatment may be obtained outside the cell environment since the membrane surface dipoles are affected by the particles. The present invention, however, also applies to affecting the dielectric, conductivity and frequency dependent dispersion curves both extracellularly as well as intracellularly (i.e., those instances where the particles are metabolized or absorbed by the cells of a host organism whether the cells are reactive, inflammatory diseased cells or normal cells).

Through the introduction of particles in the joint cells the intracellular conductivity can be altered as well as the charge accumulation on the joint cell membrane. This enhancement of conductivity as well as the alteration in membrane events allows two benefits. The alteration in cell membrane characteristics enables the delivery of energy intracellularly at a lower frequency due to the effect on the charge accumulation on the cell membrane. The increased conductivity of the joint cell allows more energy to be delivered and a better coupling at the given frequency.

In addition, the effect on the normal joint cells is greatly reduced because the energy requirements are less, the normal joint cell membrane still acts as a barrier at this frequency and the frequency to be utilized can be lowered.

Consequently, through the alteration of the intracellular environment and the membrane effects at a given frequency, more energy can be delivered to the reactive and/or inflammatory diseased joint cells, a lower frequency can be utilized since the reactive and/or inflammatory joint cell membrane will start to short out at a lower frequency and the effect on the normal cells is reduced due to its intact cell membrane characteristics.

The process of the present invention involves the use of intracellular particles in the inflammatory and reactive cells of the joint space. These particles may be introduced into the patient by intravenous, intra-arterial or intra-lymphatic injection. The particles may also be injected directly into the joint space.

The particles are of a ferromagnetic, paramagnetic, or diamagnetic nature and therefore capable of responding to an external alternating electromagnetic field. The particles, in general, are under 1 micron in size and in a colloidal-type suspension although for the direct joint injection they may be directly introduced.

In addition, any electric or magnetic dipole in the cell or capable of being induced in the cell may be utilized. A constant magnetic field can be used to induce these dipoles as well as enhance the effect of the external alternating electromagnetic field or dipoles or particles containing these dipoles which are present in the cell. This constant magnetic field can be used to help concentrate the particles in the area of the joint.

The choice of particle type, size and shape can be highly significant to effective treatment, particularly where subcellular localization or other subtle differentiations in metabolic activity, for example, are conveniently utilized to maximize particle uptake and absorption. Suitable particles and exemplifications of selection parameters are disclosed and examined in copending and commonly assigned Application Ser. No. 535,390 of the same inventor, incorporated herein by reference.

The particle systems include metalloporphyrins, $Fe_2O_3$, metal-metalloporphyrins and particularly useful particles including both inorganic elements and compounds as well as metal containing organic compounds. Inorganic elements and compounds particularly well suited, owing to their favorable magnetic parameters, comprise elements such as dysprosium, erbium, europium, gadolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$), yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series elements and compounds thereof.

Metal containing-organic molecules useful for the application described above, comprise particles of iron-dextrans such as FeOOH-dextran complexes and other dextran metal complexes wherein the metal is selected from the group comprising cobalt, iron, zinc, chromium, nickel, gallium, platinum, manganese and rare earth metals such as dysprosium, erbium, europium, gadolinium, holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and dysprosium-gallium and iron such as $Fe_2O_3$ particles, $Fe_3O_4$ particles and FeOOH particles and $Fe_2O_3$-dextran complexes, $Fe_3O_4$-dextran complexes, and Fe OOH-dextran complexes, and actinide series elements and compounds, ferric ammonium citrate, and various iron transporting and chelating compounds such as enterochelin, transferrin, etallothionein, hydroxamates, phenolates, ferrichromes, desferri-ferrichromes, ferritin, ferric mycobactins, and iron-sulfur proteins such as ferredoxin and rubredoxin and transferrin as well as transferrin compounds and complexes.

Particularly appropriate metal-containing organic structures for use with the present invention are the prophyrins such as etioporphyrins, mesoporphyrins, uroporphyrins, coproprophyrins, protoporphyrins, and dicarboxylic acid containing porphyrins and substituted porphyrins such as tetraphenylporphyrin sulfonate (TPPS). Especially advantageous protoporphyrins comprise hematoporphyrins, chlorophylls, and cytochromes. In addition to the naturally occuring protoporphyrins which possess either iron or magnesium containing moieties, mixed-metal or di-metal hybrid porphyrins may also be prepared. For example, by substituting an alternative metal for the iron in hematoporphyrin, the advantages of the porphyrin moiety (e.g., in terms of specificity of localization is retained while the unique magnetic properties of the new metal enhance the sensitivity of the substituted molecule. Suitable metals for purposes of substitution comprise cobalt, iron, manganese, zinc, chromium, gallium, nickel, platinum and rare earth series of metals such as dysprosium, erbium, europium, gadolinium holmium, samarium, terbium, thulium, ytterbium and ytterium, dimetallic compounds such as dysprosium-nickel, dysprosium-cobalt, gadolinium-iron, ytterbium-iron, cobalt-samarium, gadolinium-yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing porphyrin such as protoporphyrins (e.g., hematoporphyrins) and the like.

The substitution reaction is carried out in vitro by reacting the desired metal with the desired porphyrin in the presence of the enzyme ferrochelatase (E.C. 4.11.1.1). Reaction conditions as described by Jones and Jones (Biochem. J. 113:507-14, 1969) or Honeybourne, et al (FEBS Lett.: 98:207-10, 1979) are suitable.

Additional particle systems particularly suited to use in this present invention include $Fe_3O_4$-transferrin dextran, metal-transferrin (transition, rare-earth), metalloporphyrin-transferrin, antibody-ferritin-particles, antibody-ferritin-transferrin particles, antibody-transferrin particles, metal-porphyrin-metal complexes, metallothionein particles, and lectin particles. Useful particle systems for use in this present invention further comprise: Where particle=$Fe_3O_4$, transition metal, rare-earth metal, metalloporphyrin, etc. as well as ferromagnetic and paramagnetic particles.

One magnetic characteristic known to be temperature dependent is magnetic susceptibility. Magnetic susceptibility is measured by the ratio of the intensity of magnetization produced in a substance to the magnetizing force or intensity of the field to which it is subjected. This magnetic characteristic is routinely measured by magnetometer devices such as a vibrating magnetometer or a flux gate magnetometer. Therefore, by measuring the magnetic susceptibility of particles at various temperatures, it is quite simple to calibrate the magnetometer equipment so that when it measures the magnetic susceptibility of the particles a simple calibration will indicate the exact corresponding temperature of the particle.

By way of illustrating the increased magnetic susceptibility of some of the elements or compounds described above, the following table is provided:

| Element or Compound | Temp(K) | Mag. Sus. ($10^6$ cgs) |
|---|---|---|
| Iron Oxide (ref.) | 293 | +7,200 |
| Dysprosium Oxide | 287.2 | +89,600 |
| Dysprosium Sulfate Octahydrate | 291.2 | +92,760 |
| Erbium Oxide | 286 | +73,920 |
| Erbium Sulfate Octahydrate | 293 | +74,600 |
| Europium | 293 | +34,000 |
| Europium Oxide | 298 | +10,100 |
| Europium Sulfate | 293 | +25,730 |
| Holmium Oxide | 293 | +88,100 |
| Holmium Sulfate Octahydrate | 293 | +91,600 |
| Terbium | 273 | +146,000 |
| Terbium Oxide | 288.1 | +78,340 |
| Terbium Sulfate Octahydrate | 293 | +76,500 |
| Thulium | 291 | +25,500 |
| Thulium | 296.5 | +51,444 |
| Ytterbium Sulfide | 292 | +18,300 |

Thus, the enhanced magnetic characteristics displayed by the particles of the subject invention results in an increase in an electromagnetic field thereby increasing the overall sensitivity and control of the modalities for the improvement of the instant invention techniques and for the resultant effects.

Magnetic susceptibility has also been used heretofore in connection with the treatment protocol as disclosed in U.S. Pat. No. 4,163,683 of the same inventor, where magnetic susceptibility measurements are correlated with temperature (an interdependent variable) in accomplishing the related induction heating step controllably. There is no recognition, however, that the values for magnetic susceptibility, independent of the induction heating step or the imposition of an electromagnetic field can be usefully correlated (to maximization of particle concentration with time) to optimize treatment effectiveness, as demonstrated herein.

A further benefit is derived from the fact that some particle compositions comprise a ferromagnetic, paramagnetic, or diamagnetic component integrated into a cell or organelle specific molecular structure, thereby permitting efficient targeting and delivery of said particles to specific intracellular joint compartments such as mitochrondria, chloroplasts, nuclei, vacuoles, and the like.

In addition, particle systems which are kept outside the joint cells may be utilized to alter membrane events and affect the frequency of response and the energy transmission of the reactive and/or inflammatory diseased joint cells and the normal joint cells. In certain circumstances these particles may be utilized to stabilize the membrane of normal joint cells and decrease their response to a field at a given frequency.

A steady magnetic or electric field may be used to enhance the uptake of particles by the joint cells as well as enhancing the membrane and cytoplasmic alterations which occur and are fully disclosed and described in copending and commonly assigned Application Ser. No. 535,390 of the same inventor incorporated herein by reference. For example, the application of the localized static magnetic or electric field may occur concurrently with the application of an alternating, oscillating or pulsed electromagnetic field. That is to say, the localized static magnetic or electric field may be superimposed on the subject of interest while the alternating, oscillating or pulsed field is also being applied.

Temperature measurements are taken in living tissue of the host organism and correlating the temperature readings to the low frequency magnetic field causing alteration in dielectric properties and/or conductivity and/or frequency dependent dispersion curves. Once the temperature is correlated with these measurements, (dielectric properties, conductivity and frequency dependent dispersion curves) these measurements are then made along three axes at right angles to one another in the host organism from which a three dimensional temperature map of the body is produced by restructuring them in a three dimensional temperature model by computer processes well known in the art.

The frequency of the magnetic field is selected to enhance the dielectric properties, conductivity and electric dipoles of the joint cells and will vary depending upon the particles employed therein. The frequency, however, is adjusted so that thermal effects thereby obtained are not due to hysteresis loss from the particles themselves but rather the alteration in conductibility, dielectric properties and electric dipoles of the joint cells that are brought about by the use of the particles of the present invention. Generally, the range of frequencies that may be employed will be anywhere from about 1 Hz to about 500 MHz: 1 Hz to about 100 MHz; 1 Hz to less than 13 MHz; 1 Hz to about 100 KHz; 1 hertz up to less than 50 kilohertz and especially from about 10 hertz up to about less than 50 kilohertz as well as any frequency within these ranges or range of frequencies within the aforesaid ranges.

The present invention, therefore, will be practiced at the above frequencies and the copending applications incorporated herein by reference will give the person of ordinary skill in the art a disclosure of how to practice the present invention with the exception that the frequencies described above will be employed in lieu of those utilized in such copending applications.

To further illustrate the operation of this instant invention, the following treatment scenario is provided.

Reference herein to tissue, organ or cell population is intended in its most embracive and comprehensive sense, referring in general to the region of the host organism affected by the invasive abnormality, or the treatment region, as the context requires.

The subject receives an intravenous injection or direct injection of colloidally suspended particles such as iron porphyrin (FeTPPS$_4$) at a dosage of 2-10 mg/kg. After a prescribed period of time which is dependent on the method of introduction of the particles i.e. after 24-72 hours after intravenous injection and 2-8 hours after direct injection, the subject is exposed to an alternating electromagnetic field at a frequency of 1 Hz to 100 MHz in this case 500 Hz for a period of approximately 10-20 minutes. The alternating electromagnetic field may be applied via a coil arrangement or via capacitor plates or via electrodes in the tissue or any suitable means available in the state of the art, and consistent in application to this present invention. The process may be repeated as is necessary.

This field supplies energy to the interior of the joint cells thereby affecting only the reactive and/or inflammatory diseased joint cells and not the normal cells. The amount of energy can be precisely controlled to affect only the reactive and/or inflammatory diseased joint cells and not the normal cells.

In summary, the introduction and absorption of minute particles into the joint cell alters the intracellular environment and the charge accumulation on the membrane. Consequently, lower power levels may be used to transmit energy into the joint cell, lower frequencies may be used because of the alteration in membrane events and the effect on normal cells is greatly reduced because of the above as well as the state of the normal joint cell's membrane. In addition, modification can be performed by using particles to alter the extracellular environment as well.

In addition, since radiofrequency fields can affect particles by causing reversible or irreversible changes in the particles, i.e. magnetostrictive induced vibrations, by affecting the particles with an alternating electromagnetic field in the range 1 Hz to 500 MHz either prior or during treatment, the particles can be made more or less responsive to the field. This alternating field can produce acoustic changes in the particle and affect the joint cell and subcellular structures.

As disclosed by the applicant in his U.S. Pat. No. 4,136,683 and as disclosed in copending and commonly assigned Application Ser. No. 535,390 (C.I.P. to Application Ser. No. 522,941) of the same inventor and incorporated herein by reference, this present invention can be used to create a three-dimensional temperature map of the body. In addition, the measurements of these properties allows one to follow the distribution of the particles in the body by following the change in the dielectric properties, conductivity, and frequency dispersion curves both before and after ingestion up of the particles.

Molecules in a joint cell can be affected if $\mu\beta > kt$ (where u is dipole moment, $\beta$ is the field strength, k is the Boltzman constant, and $\tau$ is absolute temperature). Consequently by introducing the particles and increasing the relative dipole moment in the joint cell the direct effects on molecules in the joint cell can be enhanced even beyond thermal effects. Therefore, this present invention may directly affect the molecules in the joint cell.

Through these processes the dielectric properties across the membrane can be affected including the stimulation and/or alteration of nerve impulses and/or electrical events.

The ionic environment around the surface of the particle by becoming polarized can produce increased dielectric properties as well. In addition, membrane effects with the anionic proteinaceious material which accumulates around the joint cell can produce local effects.

When you have a mixture with different dielectric properties relaxation phenomenon will occur not at a single frequency, but over a wide range of frequencies. The curve is broadened due to interactions in the mixture. Inclusion of material of low dielectric constant will lower the dielectric constant of the mixture. Therefore, the addition of particles to the inside of the joint cell broadens the frequency response of intracellular structures as compared to the other cells and structures. Particle geometry also affects the frequency response. Consequently, the presence of the particles allows for a differential affect on subcellular structures.

Through the use of magnetic susceptibility measurements as described in the Applicant's U.S. Pat. No. 4,136,683 and as disclosed in copending and commonly assigned Application Ser. No. 535,390 (C.I.P. to Application Ser. No. 522,941) and as disclosed in copending and commonly assigned Application Ser. No. 627,536 of the same inventor and incorporated herein by reference, the uptake of particles in the joint and joint space can be followed as a function of time. This may be used diagnostically to evaluate which joints are affected by the disease process by analyzing which joint takes up the particles. The magnetic characteristics of the particle in the joint cell can be used to help diagnose which disease process is present in the joint. Magnetic mapping techniques can also be used.

The process of this present invention is further illustrated by the following examples:

EXAMPLE I

A colloidal solution of $Fe_3O_4$-dextran-transferrin is prepared in a concentration of 20 mg/cc in Rogers lactate. An intravenous injection of 2 cc is performed slowly over a period of 5 minutes. Over the next 48-72 hours, periodic measurements of magnetic susceptibility using a SQUID magnetometer as well as magnetic mapping measurements are performed. This allows identification of the joints which are involved, as well as helping to determine the type of disease process and the point in time of maximum uptake of the particles. At this time, the patient is subjected to the alternating electromagnetic field which destroys the reactive and/or inflammatory diseased cells in the joint and inhibits the pannus formation. Any diseased joint in the body can be treated by this process.

EXAMPLE II

A colloidal suspension of $FeTPPS_4$-acetate 20 mg/cc in Rogers lactate is injected directly into the joint (2 cc injection). A strong constant magnetic field is applied to concentrate the particles in the joint and to increase the dipole which are present to enhance the effect of the alternating electromagnetic field. After 4 hours the joint is placed within a coil and an alternating electromagnetic field is applied. This field is applied until an energy rise of 8-10 C is achieved in the reactive and/or inflammatory diseased joint cells with resultant destruction of these cells and modification of the degenerative process.

What is claimed is:

1. A process for the treatment of arthritis and other non-infections joint diseases by affecting particles present and/or introduced intracellularly into reactive and/or inflammatory diseased cells in the joint and joint space without substantially damaging normal cells,
   providing to said host joint minute particles capable of being taken up by said reactive and/or inflammatory diseased joint cells,
   allowing said particles to effect at least one event comprising intracellular events and membrane events in said reactive and/or inflammatory diseased cells in the joint space and area,
   subjecting said joint space and area to a relatively low frequency alternating, oscillating and/or pulsed electromagnetic field to provide energy to reactive and/or inflammatory diseased cells and selectively heat said reactive and/or inflammatory diseased joint cells.

2. The process of claim 1 including the utilization of magnetic or electric dipoles present or capable of being induced in the joint or in the reactive and/or inflammatory diseased cells of the joint or in the joint space.

3. The process of claims 1 or 2 wherein particles are introduced intravenously, intra-arterially, or intra-lymphatically.

4. The process of claims 1 or 2 wherein particles are introduced directly into the joint and/or joint space.

5. The process of claims 1 or 2 wherein particles are ferromagnetic, paramagnetic or diamagnetic.

6. The process of claims 1 or 2 wherein particles are colloidally suspended and under one micron in size.

7. The process of claims 1 or 2 wherein said particles are selected from the group consisting of ferromagnetic, paramagnetic and diamagnetic elements, inorganic compounds, organic compounds and combinations thereof metalloporphyrins, $Fe_2O_3$, FeOOH, and metal metalloporphyrins.

8. The process of claim 7 wherein said particles are selected from the group consisting of
   (a) cobalt, zinc, iron, chromium, nickel, platinum, rare earth metals consisting of dysprosium, erbium, europium, gadolinium, holmium, samarium, terbium, thulium, ytterbium, yttrium and compounds thereof consisting of dysprosium sulfate, erbium sulfate, europium oxide, europium sulfate, gadolinium oxide, gadolinium sulfate, holmium oxide, samarium sulfate, terbium sulfate, thulium oxide, ytterbium sulfide, yttrium oxide, yttrium sulfate, yttrium ferrioxide ($Y_3Fe_5O_{12}$), yttrium oxide ($Y_3Al_5O_{12}$), dysprosium-nickel, ysprosium cobalt, gadolinium-iron, ytterbium-iron, cobalt-samarium, gadolinium-ytterbium, dysprosium-gallium, and actinide series elements and compounds thereof; and combinations thereof.

9. The process of claim 7 wherein said organic compounds are selected from the group consisting of;
   (a) dextran metal complexes wherein said metal is selected from the group consisting of cobalt, zinc, chromium, iron, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium, and iron consisting of $Fe_2O_3$ particles, $Fe_3O_4$ particles and FeOOH particles and $Fe_2O_3$-dextran complexes, $Fe_3O_4$-dextran complexes, and FeOOH-dextran complexes;
   (b) iron transporting and chelating compounds consisting of ferric ammonium citrate, enterochelin, transferrin, metallothionein, hydroxamates, phenolates, ferrichromes, desferriferrichromes, ferritin, ferric mycobactins and iron sulfur proteins consisting of ferredoxin and rubredoxin;
   (c) porphyrins comprising etioporphyrins, meso-porphyrins, uroporphyrins, coproporphyrins, protoporphyrins, dicarboxylic acid containing porphyrins, substituted porphyrins consisting of tetraphenylporphyrin sulfonate and protoporphyrin containing molecules consisting of hematoporphyrins, chlorophylls, and cytochromes;
   and combinations thereof.

10. The process of claim 9 wherein said prophyrin is one in which the natural occurring metal moiety is substituted with a metal selected from the group consisting of cobalt, zinc, chromium, gallium, iron, manganese, nickel, platinum, dysprosium, erbium, europium, gadolinium, holmium, samarium, terbium, thulium, ytterbium, yttrium, dysprosium-nickel, dysprosium-cobalt, gadolinium-iron, yttrebium-iron, cobalt-samarium, gadolinium-yttrium, and dysprosium-gallium;
    and combinations thereof.

11. The process according to claims 9 or 10 wherein said iron transporting, iron chelating and porphyrin compounds are chemically complexed with dextran.

12. The process according to claim 11 wherein said composition is chemically complexed with an antibody.

13. The process according to claim 9 wherein the metal-organic compound complexes are selected from the group consisting of Fe(III) Tetraphenylporphyrin sulfonate (TPPS$_4$) Acetate, Fe(III) TPPS$_4$ Acetate 4Na Salt (H$_2$O), Fe(III) Mesoporphyrin IX Chloride, Fe-(III) TPPS$_4$Chloride, Co TPPS$_4$, Co(III) MesoTPPS$_4$ Tetra Na Salt (Acetate), Fe Phthalocyanine Tetrasulfonate Tetra sodium salt, Tetra Sodium-meso-Tetra (4-sulfonate-phenyl) Porphine (12 hydrate), Fe(III) Tetra (N-Methyl 4-Puridyl) Porphyrin Pentachloride, Fe Phthalocyanine, Hemin, Fe-Hematoporphyrin D (HPD), Fe-Acetoxyethyl vinyl Deuteroporphyrin, Fe-Protoporphyrin IX, Fe-Deuteroporphyrin 2, 4 bis acetal, Mn-TPPS$_4$, Co-N+MTPyP, Mn-N+MTPyP, Co-Mesoporphyrin X, Protohemin, Deuterohemin, Mesotetra (4-N methyl pyridyl) hemin tetraiodide, Mesotetra (4-carboxy phenyl) hemin, Ni-TPPS, Ni-HPD, Mn-mesoporphyrin IX, Co-Protoporphyrin IX, Mn-Protoporphyrin IX, Sn-Protoporphyrin IX, Co-HPD, Mn-HPD, Gd-TPPS, Gd-HPD, Hematoporphyrin Mono-acetate-Fe, Ferretin-Fe, Ferredoxin-Fe(4), Transferrin-Fe, Hematoporphyrin Diacetate-Gd, GdFe-TPPS$_4$, GdFe$_2$-HPD, FeTPPS$_4$(OH$_2$)$_2$ClO$_4$-, FeTPP (OH$_2$)$_2$ ClO$_4$-, Fe-Nitrolacetate, Fetetrasulfinated phalocyanine, Bisimidozole (FeTPPS)ClO$_4$-, Rubrium-ferricytochrome/C, and combinations thereof.

14. The process according to claim 13 wherein said metal-organic compound complexes are chemically complexed with dextran.

15. The process according to claim 14 wherein said composition is chemically complexed with an antibody.

16. A process for affecting molecules in the joint cell and subcellular structures in the tissue of a host organism comprising applying a constant magnetic field to said tissue to affect the relative dipole moment and producing direct effects on subcellular structures and molecules in the cells of said tissue by introducing particles into the living cells of said tissue.

17. The process of claim 16 wherein the constant magnetic field is initially utilized and thereafter applying an alternating electromagnetic field to achieve an enhanced effect.

18. A process for the diagnosis of non-infectious joint disease through the use of intra-articular particles which may be intracellular in the cells contained in the joint.

19. The process of claim 1 wherein magnetic susceptibility measurements are performed to diagnose the involved joints by the uptake of the particles.

20. The process of claim 1 wherein magnetic mapping measurements are performed to diagnose the involved joints.

21. The process of claim 20 wherein magnetic susceptibility measurements are performed to determine the optimum time of treatment.

22. The process of claim 19 wherein magnetic susceptibility and magnetic mapping measurements are performed to help diagnose the type of disease process present in the joint.

23. The process of claim 1 or 2 comprising applying a localized static magnetic or electric field to joint tissue to aid in the intracellular uptake and energy absorption of the electric or magnetic dipoles either introduced or already present in said joint.

24. The process of claims 1 and 2 wherein a localized static magnetic or electric field is applied to said joint after providing said particles but prior to or during the application of said alternating, oscillating and/or pulsed electromagnetic field to enhance the intracellular uptake of energy and the energy-absorption responsiveness of said particles in joint.

25. The process of claim 17 wherein a localized static magnetic or electric field is applied to the joint prior to and/or during the application of said alternating, oscillating and/or pulsed electromagnetic field to enhance the intracellular energy uptake and energy absorption of the electric or magnetic dipoles either introduced or already present in the joint.

26. The process of claims 1 or 2 wherein a constant magnetic field through interaction with intracellular dipoles in the joint is utilized to modify the behavior of the reactive and/or inflammatory diseased cells of the joint to slow the degenerative process.

27. The process of claim 16 wherein the static magnetic or electric field is between 100 gauss and 80 kilogauss.

28. The process of claims 1 or 2 wherein said alternating, oscillating and/or pulsed electromagnetic field is between 1 Hz to about 100 MHz.

29. The process of claims 1 or 2 including an external alternating electromagnetic field applied to excite the particles and raise the energy level in the reactive and-/or inflammatory diseased cells of the joint to destroy said joint cells or modify their behavior to decrease the joint degenerative process.

30. The process of claims 1 or 2 wherein the treatment is continued to attain an increase of intracellular temperature of between 8 Centigrade and 100 Centigrade to modify, alter, and/or kill the reactive and/or inflammatory diseased cells of the joint.

31. The process of claims 1 or 2 wherein particles are introduced into the extracellular environment of said joint tissue to alter membrane events and potentiate energy delivery to said diseased inflammatory and/or reactive joint cells and/or reduce energy delivery to said normal joint cells.

32. The process of claims 1 or 2 wherein particles are introduced intravenously, intra-arterially, intra-lymphatically, and/or locally, for ultimate delivery to the reactive and/or inflammatory diseased cells of the joint.

33. The process for measurement of temperature in living tissue and cells in the joint comprising measuring the alteration in dielectric properties, conductivity and frequency dependent dispersion curves in living joint tissue and cells with temperature.

34. The process of claim 33 comprising measuring said temperature along three axes at right angles in a host joint organism and producing a three-dimensional temperature map of the body from said measurements.

35. A process to measure the change in metabolism in living joint cells comprising measuring the alteration in dielectric properties of said joint cells and correlating said measurements with metabolism in said joint cells.

36. A process to follow the exact distribution of particles in living joint tissue and cells comprising measuring the alteration in dielectric properties, conductivity and frequency dependent dispersion curves of said tissue and joint cells with the introduction of particles into said tissue and joint cells.

37. A process of claims 1 or 2 for affecting intracellular and extracellular events comprising subjecting said particles to ultrasound, said particles being selected to enhance the effect of ultrasound on said joint tissue and cells.

38. A process of claim 7 for affecting intracellular and extracellular events comprising subjecting said particles to ultrasound, said particles being selected to enhance the effect of ultrasound on said joint tissue and joint cells.

39. The process of claims 1 or 2 wherein an alternating electromagnetic field between 1 Hz and 500 MHz is used to affect said particles and make them more or less responsive to an exciting alternating electromagnetic field produced by magnetostrictive induced vibrations applied to said joint tissues and joint cells.

40. The process of claim 7 wherein said particles are selected to include compositions that specifically affect intracellular and extracellular events in said joint tissues and tissue cells or said particles are affected to make them more or less responsive to an exciting alternating electromagnetic field produced by magnetostrictive induced vibrations.

41. The process of claims 1 or 2 wherein an alternating electromagnetic field is applied to said particles to produce acoustic changes in said particles and affect the cellular and subcellular structures of said joint tissues and/or joint cells.

42. The process of claim 7 wherein said particles are selected to acoustically affect intracellular and extracellular events in said joint tissues and joint cells or said particle and affecting the cellular and subcellular structures of said joint tissues and joint cells.

43. The process of claims 1 or 2 wherein magnetic susceptibility measurements are performed to diagnose the involved joints by the uptake of the particles.

44. The process of claims 1 or 2 wherein magnetic mapping measurements are performed to diagnose the involved joints.

45. The process of claim 44 wherein magnetic susceptibility measurements are performed to determine the optimum time of treatment.

46. The process of claim 43 wherein magnetic susceptibility and magnetic mapping measurements are performed to help diagnose the type of disease process present in the joint.

47. The process of claim 44 wherein magnetic susceptibility and magnetic mapping measurements are performed to help diagnose the type of disease process present in the joint.

48. The process of claim 17 wherein a localized static magnetic or electric field is applied to the joint prior to and/or during the application of said alternating, oscillating and/or pulsed electromagnetic field to enhance the intracellular energy uptake and energy absorption of the electric or magnetic dipoles either introduced or already present in the joint.

49. The process of claim 23 wherein a localized static magnetic or electric field is applied to the joint prior to and/or during the application of said alternating, oscillating and/or pulsed electromagnetic field to enhance the intracellular energy uptake and energy absorption of the electric or magnetic dipoles either introduced or already present in the joint.

50. The process of claim 16 wherein the static magnetic or electric field is between 100 gauss and 80 kilogauss.

51. The process of claim 17 wherein the static magnetic or electric field is between 100 gauss and 80 kilogauss.

52. The process of claim 23 wherein the static magnetic or electric field is between 100 gauss and 80 kilogauss.

53. The process of claim 24 wherein the static magnetic or electric field is between 100 gauss and 80 kilogauss.

54. The process of claim 25 wherein the static magnetic or electric field is between 100 gauss and 80 kilogauss.

55. A process for the treatment of arthritis and non-infections joint diseases comprising:
introducing into the joint or joint space minute particles capable of being taken up by the reactive and/or inflammatory diseased joint cells and of responding to a relatively low frequency electromagnetic field, and
after said introducing, subjecting the joint or joint space to a relatively low frequency electromagnetic field having a frequency of less than 500 megahertz to energize and selectively heat said reactive and/or inflammatory diseased cells without substantially damaging the normal cells.

56. The process of claim 50 including,
said subjecting including said frequency being selected to enhance the dielectric properties, conductivity and electric dipoles of the joint cells.

57. The process of claim 50 including,
said subjecting including said field having a frequency between 1 hertz and 100 megahertz.

58. The process of claim 50 including,
said subjecting including using capacitor plates to generate said field.

59. The process of claim 50 including,
said subjecting including using a coil arrangement to generate said field.

60. The process of claim 50 including,
said subjecting including using electrodes to generate said field.

61. The process of claim 50 including,
said subjecting including said field being an alternating electromagnetic field.

62. The process of claim 50 including,
said subjecting including said field being an oscillating electromagnetic field.

63. The process of claim 50 including,
said subjecting including said field being a pulsing electromagnetic field.

64. The process of claim 50 including,
before said subjecting, allowing said particles to effect at least one event comprising intracellular events and membrane events in said reactive or inflammatory diseased cells.

65. The process of claim 50 including,
said introducing including said particles being introduced intravenously.

66. The process of claim 50 including,
said introducing including said particles being introduced intra-arterially.

67. The process of claim 50 including,
said introducing including said particles being less than one micron in size and colloidally suspended.

68. The process of claim 50 including,
said introducing including said particles being absorbed into the joint cell and altering the intracellular environment and the charge accumulation on the membrane.

69. The process of claim 50 including, said introducing including said particles being ferromagnetic, paramagnetic, or diamagnetic.

70. The process of claim 50 including,
said introducing including said particles being introduced directly into the joint and/or joint space.

71. The process of claim 50 including,
said introducing including introducing said particles into the extracellular environment of the joint tissue.

72. The process of claim 50 including,
after said introducing and before said subjecting, evaluating which joints are affected by the disease process by analyzing which joint takes up said particles.

73. The process of claim 73 including,
said analyzing including using magnetic susceptibility measurements.

74. The process of claim 50 including,
imparting a dipole to said particles before said subjecting step.

75. The process of claim 50 including,
applying a constant magnetic field to the joint before said subjecting step.

76. The process of claim 75 including,
said subjecting including said field being an alternating electromagnetic field.

77. The process of claim 50 including,
performing magnetic susceptibility measurements to determine the optimum time of said subjecting step.

78. The process of claim 50 including,
performing magnetic susceptibility and magnetic mapping measurements to help diagnose the type of disease process present in the joint.

79. The process of claims 1, 16, 19, 36 or 55 wherein the particles are metal containing organic molecules.

80. The process of claims 1, 16, 19, 36 or 55 wherein the particles are iron containing organic molecules.

* * * * *